United States Patent [19]

Hanson

[11] 4,248,588
[45] Feb. 3, 1981

[54] ORTHODONTIC BRACKET AND ARCH WIRE

[76] Inventor: Gustaf H. Hanson, 33 Woodside Dr., Hamilton, Ontario, Canada, L8T 1C4

[21] Appl. No.: 34,457

[22] Filed: Apr. 27, 1979

Related U.S. Application Data

[63] Continuation-in-part of Ser. No. 886,274, Mar. 13, 1978, abandoned.

[51] Int. Cl.$^3$ ................................................ A61C 7/00
[52] U.S. Cl. ...................................................... 433/11
[58] Field of Search ..................................... 433/11, 13

[56] References Cited

U.S. PATENT DOCUMENTS

| | | | |
|---|---|---|---|
| 3,772,787 | 11/1973 | Hanson | 433/11 |
| 4,068,379 | 1/1978 | Miller | 433/9 |
| 4,144,642 | 3/1979 | Wallshein | 433/11 |

*Primary Examiner*—Robert Peshock
*Attorney, Agent, or Firm*—Hirons, Rogers, Scott

[57] ABSTRACT

A new orthodontic bracket comprises a bracket body (20) with a mesial-distal slot (42) for the reception of an arch wire (46 or 80) and a resilient retainer member (48) for retaining the arch wire in the slot, the retainer member being movable on the bracket body in the occlusal-gingival directions between s slot-closed position (e.g. FIG. 5) and a slot-open position (e.g. FIG. 4). The part (50) of the retainer member which closes the slot has its free end extending into the slot, so that movement of the retainer member out of the slot-closed position takes place against its resilience as the opposed embracing retainer parts are moved apart. Moreover, any force urging the arch wire out of the slot and contacting it with the retainer urges the retainer to the slot-closed position. In the slot-open position the retainer member can be "parked" on a mesial-distal extending parking land (70) on the bracket body. A labial-extending gingival step surface (60) is provided to determine the slot-closed position and to shield the adjacent bottom edge of the retainer member. The lingual end (52) of the retainer member protrudes into a recess (66) in the base, the shape of the recess enabling the member to be moved from slot-closed to slot-open position by inserting a suitable tool into the recess. A new arch wire (80) for use with such an orthodontic bracket has a convex curved labial face (82) and a lingual face (88) that is lingually inclined in the direction from the gingval face to the occlusal face to form a wedge shaped profile, the wire receiving slot (42) having a complementary cross-section. Such a wire provides better control of torque, while at the same time the bracket is usable with a round arch wire (46).

16 Claims, 14 Drawing Figures

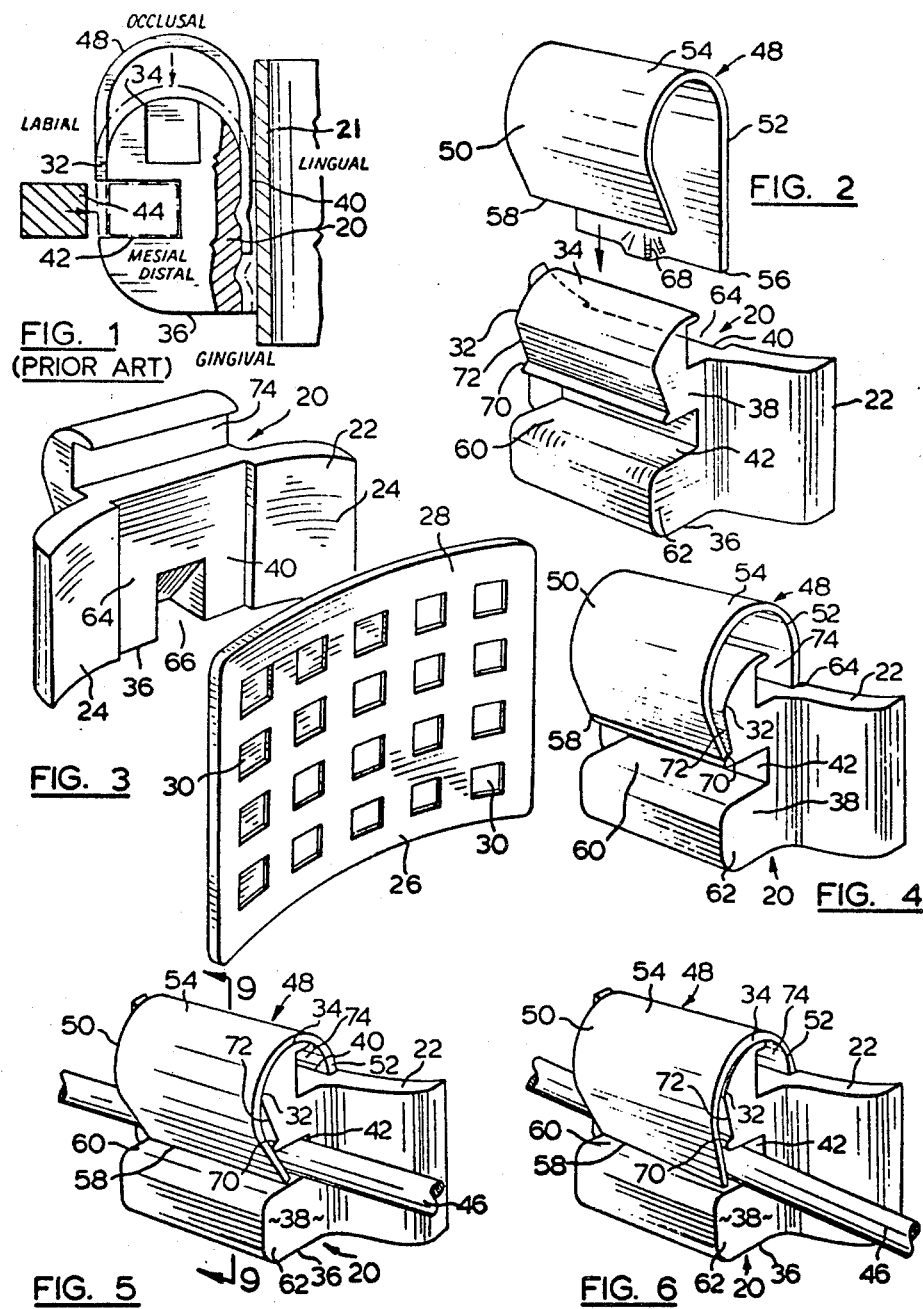

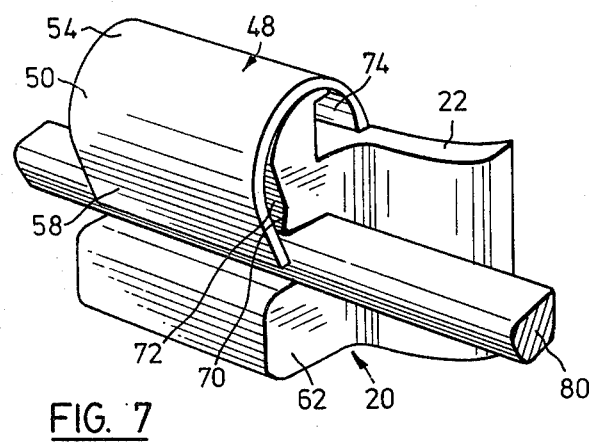
FIG. 7
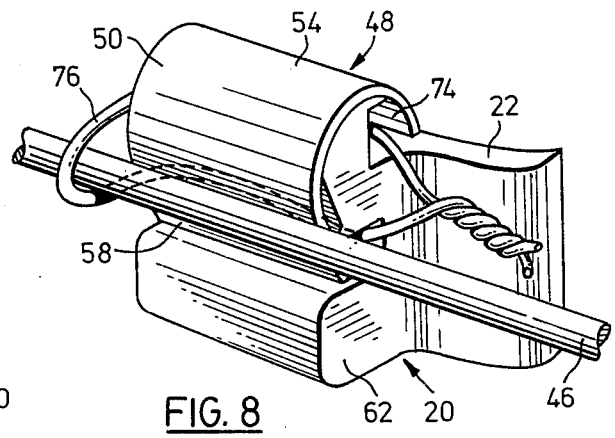
FIG. 8
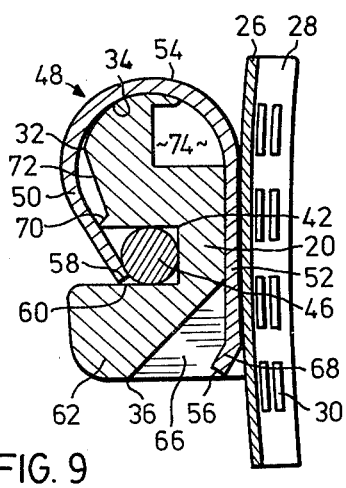
FIG. 9
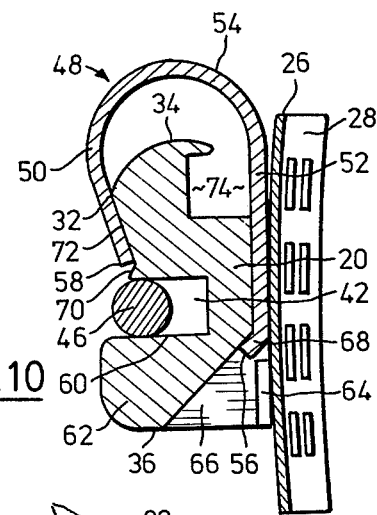
FIG. 10
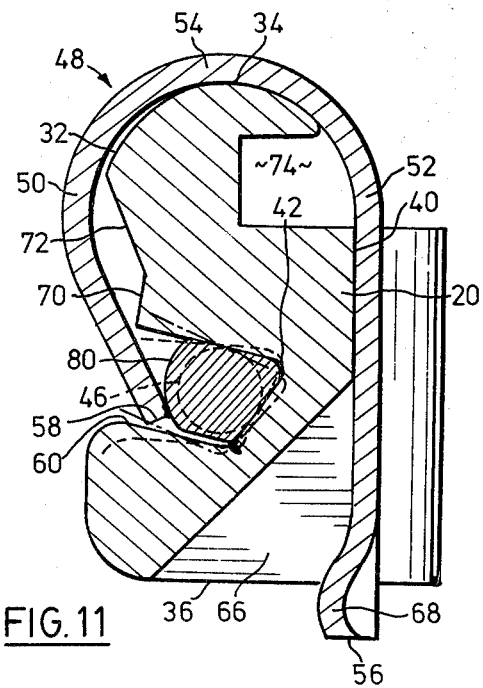
FIG. 11
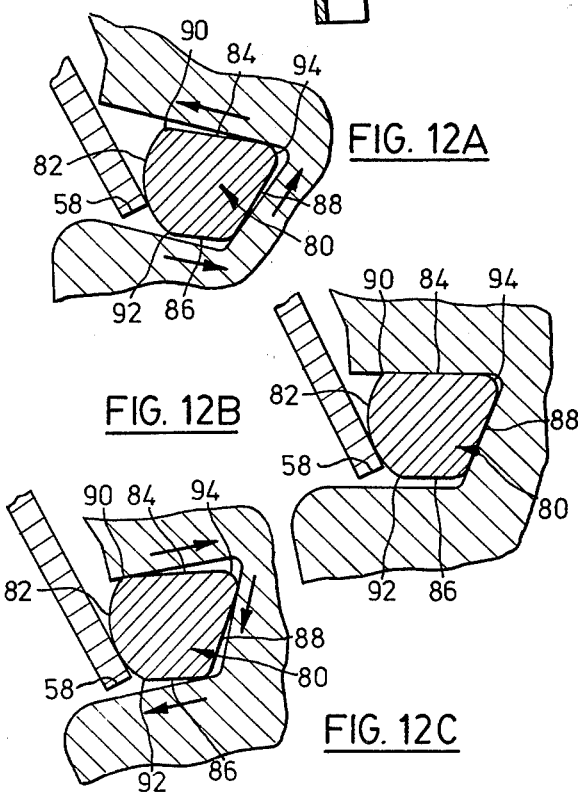
FIG. 12A
FIG. 12B
FIG. 12C

ORTHODONTIC BRACKET AND ARCH WIRE

CROSS REFERENCE TO RELATED APPLICATION

The present application is a continuation-in-part of my earlier application Ser. No. 886,274 filed 13th Mar. 1978 now abandoned.

The present invention is concerned with improvements in or relating to orthodontic brackets that are employed in procedures for applying corrective moving forces to teeth. The invention is also concerned with improvements in or relating to arch wires for use with such a bracket.

It is now almost universal practice in orthodontic procedures that each tooth to be moved has a bracket fastened thereto, the brackets being connected together by a thin springy arch wire that applies the required forces thereto. The bracket is usually fastened to a tooth band that is mounted around the tooth but increasingly, with the development of suitable cement systems, the brackets are cemented directly to the tooth surfaces by means of a bonding pad.

There is disclosed and claimed in my U.S. Pat. No. 3,772,787, issued 20th Nov. 1973, the disclosure of which is incorporated herein by reference, an orthodontic bracket comprising a bracket body having base, gingival, labial, occlusal, distal and mesial surface portions and a mesial-distal extending arch wire slot opening to the labial surface portion; a retainer member mounted on the bracket body, the retainer member having two opposed portions thereof in embracing sliding engagement with corresponding body surface portions with a portion thereof shaped to extend over the labial surface portion to close the corresponding side of the arch wire slot for retention of the wire therein, the retainer member being movable with said embracing sliding engagement on the body between two positions in which the slot labial side opening is respectively open and closed; and means for positively retaining the member in at least the said slot closed position.

It is an object of the present invention to provide a new orthodontic bracket that is an improvement over that disclosed in my earlier patent.

In accordance with the present invention there is provided a new orthodontic bracket comprising a bracket body having lingual, labial, gingival, occlusal, distal and mesial surface portions and a mesial distal arch wire slot opening to the labial surface portion, and a retainer member of resilient material having opposed labial and lingual portions thereof in embracing sliding engagement with corresponding labial and lingual body surface portions the retainer member being movable on the body between two positions in which the labial side of the slot is respectively open and closed, characterized in that the retainer member labial portion is so shaped that in the slot-closed position it extends over the body labial surface portion and has its free end protruding into the arch wire slot so as to engage an arch wire therein and urge it towards the lingual and occlusal walls of the slot, movement of the retainer member away from the slot-closed position toward the slot-open position taking place against the resilience of the retainer member owing to movement apart of the said opposed portions thereof in moving the said free end of the protruding labial portion out of the arch wire slot.

There is also provided an orthodontic arch wire for use in combination with such an orthodontic bracket, in which the mesial-distal extending arch wire receiving slot has parallel occlusal and gingival faces and a lingual face that is inclined lingually in the gingival to occlusal direction, the arch wire having a convex curved labial face, and having a lingual face that is lingually-inclined in the direction from the gingival face to the occlusal face to form a wedge-shaped profile at the junction of its lingual and occlusal faces.

The use of the brackets of the invention is found to result in greatly expedited procedures, owing to the elimination of the previously-used tie wires that must be individually tied in the mouth and severed. Changes in arch wire are also greatly expedited, since they require merely the retainer members to be snapped to the open position, the wire changed, and then the retainer members to be returned to the closed position, so that there is a corresponding marked reduction in patient discomfort. There is also a considerable reduction in the amount of manual dexterity required of the orthodontist in the performance of these procedures, the elimination of the need for chair-side assistance, as well as the considerable saving of time resulting in greater productivity. A cosmetic advantage is also obtained in that it has been found the brackets can be made smaller than hitherto which, together with the elimination of the somewhat unsightly and potentially uncomfortable tie wires, results in an improved appearance of the patient.

Particular preferred embodiments of the invention will now be described, by way of example, with reference to the accompanying diagrammatic drawings wherein:

FIG. 1 is a side elevation with part broken away of my prior bracket construction, as shown and claimed in my U.S. Pat. No. 3,772,787, FIG. 2 is an exploded perspective view of a bracket which is a first embodiment of the present invention, FIG. 3 is an exploded view of the bracket body of the embodiment of FIG. 2, together with an attachment pad employed in securing the bracket to a tooth by cementing, FIG. 4 is a view similar to FIG. 2 showing the bracket assembled and with the retainer member in the slot-open position, FIG. 5 is a view similar to FIG. 4 showing the retainer member in the slot-closed position and with an arch wire fully retained in the slot, FIG. 6 is a view similar to FIG. 5, showing the effect on the retainer member of an arch wire that cannot be fully retained in the slot as shown in FIG. 5, FIG. 7 shows the use of the bracket with a rectangular arch wire of the invention in the slot, FIG. 8 shows the manner in which the bracket of the invention is employed with a tie wire when the arch wire is entirely outside the slot, FIG. 9 is a vertical cross-section taken on the line 9—9 of FIG. 5, with a cementing attachment pad in position, FIG. 10 is the same cross-section as in FIG. 9, but with the retainer member in the slot-open position, FIG. 11 is another vertical cross-section of a further embodiment intended for use with a rectangular cross-section arch wire of the invention showing in broken lines modifications made thereto to adapt it for moving a tooth to a predeterminate inclined angle, and illustrating the manner in which it can be used in combination with an arch wire of circular cross-section.

FIG. 12A shows the combination of a bracket of FIG. 11 with a new rectangular cross-section arch wire of the invention employed for applying positive torque to a tooth about the mesial-distal axis, FIG. 12B is similar to FIG. 12A and shows the combination employed when no mesial-distal torque is required, and FIG. 12C is similar to FIGS. 12A and 12B and shows the combination employed for applying negative torque to the tooth about the mesial-distal axis.

Similar parts are given the same reference number in all the figures of the drawings.

Each bracket comprises a body 20 which must be mounted on the respective tooth, either by attaching it to a tooth-embracing band 21, as shown with the prior art embodiment of FIG. 1, or by cementing it directly to the tooth. Thus, the body is provided with oppositely-extending flanges 22 so as to have a sufficiently large lingual surface 24 (FIG. 3) for secure fastening of the bracket, for example by welding, to the tooth embracing band, or to a cementing pad 26, illustrated in FIGS. 3, 9 and 10. The cementing pad covers the bracket lingual surface 24 and in turn provides a lingual surface 28 which is formed in some suitable manner, e.g. of foil mesh, or by having recesses 30 formed therein, to facilitate adherence of the cement.

For convenience in description the exterior surface of the bracket body 20 is regarded as comprising a labial surface portion 32, occlusal and gingival surface portions 34 and 36 respectively connected by the labial portion, and two spaced mesial-distal surface portions 38, also connected by the labial portion. A lingual surface portion 40 oposite to the labial portion also joins the occlusal and gingival portions and the two mesial-distal portions. It will be understood that the body surface may be so smoothly contoured that adjoining surface portions merge with one another with no specific demarcation junction between them.

The body is provided with a mesial-distal-extending slot 42 of rectangular cross-section opening in the labial surface portion 32 and receiving an arch wire. In the prior art drawing FIG. 1 and in FIGS. 7 and 12 a rectangular cross-section arch wire 44 is illustrated, while the wire 46 shown in FIGS. 5, 6 and 8 to 11 is of circular cross-section. It is of course part of the expertise of the orthodontist to select a wire of appropriate cross-section and dimension from the many different ones available, depending upon the forces that are required to be applied to the tooth to be moved.

Means for retaining the arch wire in the slot, while permitting relative movements in the required directions between the bracket and the arch wire, comprise a retainer member 48 of thin flat resilient material, usually stainless steel, shaped to embrace the body 20 and to conform closely while in the slot-closed position with the labial, occlusal and lingual portions thereof. For convenience in description the retainer member will be regarded as comprising opposed labial and lingual portions 50 and 52 respectively, each in embracing sliding engagement with the respective bracket body portion, and a connecting occlusal portion 54. As with the body, these different portions of the retainer member merge smoothly into one another with no specific line of demarcation between them. The retainer member is movable by sliding and embracing movement on the body between a slot-open position illustrated in FIGS. 4 and 10 and a slot-closed position illustrated in FIGS. 5 to 9 and 11. In the prior art FIG. 1 the retainer member is shown in broken lines in slot-closed position and in solid lines in slot-open position.

In the embodiments illustrated the retainer member lingual portion 52 is relatively straight and terminates in a free end 56, while the occlusal portion is approximately semi-circular. The labial portion 50 immediately adjacent to the occlusal portion is concave toward the body in conforming closely thereto as described, while the remaining portion that terminates in a free end 58 is relatively straight and protrudes deeply into the slot 42. In the slot-closed position the free end 58 abuts against a long gingival wall 60 of the slot 42, this long gingival wall being provided by a labially-extending portion 62 of the body projecting from the body below the slot on the gingival side thereof. It will be seen that in the slot-closed position the straight part of the retainer member labial portion protrudes progressively deeper into the slot in the occlusal to gingival direction, and the extent of this protrusion is made such that it will abut firmly against an arch wire of circular cross-section of diameter for which the slot is intended. As the result of this relatively deep protrusion into the slot, any movement of the retainer member away from the slot-closed position can only take place against the resilience of the retainer member, particularly of the labial and occlusal parts thereof, owing to the need for the straight labial portion and the opposed lingual portion to move apart from one another in sliding over the body part which they embrace.

Therefore, the resilience of the springy material of the retainer member provides a force at all times urging the retainer member to move to the slot-closed position, where the free edge 58 contacts the slot gingival wall 60. The lingual portion 52 of the retainer member moves in a slot 64 in the bracket lingual surface, and a recess 66 connecting with the slot opens to the bracket lingual and gingival surfaces. The free retainer member end 56 has a part 68 thereof struck out of its general plane, so that the part cannot enter the slot 64, but can move freely in the recess 66 during movement of the member between its two extreme positions. The maximum movement of the retainer member away from slot-closed position is therefore determined by engagement of the part 68 and the bracket body at the junction of the recess and the slot. It will be seen that the retainer member can readily be moved out of slot-closed position by the orthodontist inserting a simple pusher tool into the recess to engage the part 68 and push it upwards to the maximum extent. The tool can be for example a plaque scaler, which is always available in a dental operatory.

In the full slot-open position illustrated by FIGS. 4 and 10 the labial retainer member free end 58 sits on a mesial-distal extending so-called "parking" land 70. This land is a discontinuity in the labial surface portion and is disposed at such an inclination to the remainder of the surface that any force component caused by the retainer member resilience and tending to urge the member to the slot-closed position is not able to move the end off the parking land, so that the member is retained sufficiently securely in the slot-open position. Usually the land will be located to correspond with the maximum slot-open position set by the part 68, as described above. it will usually be sufficient to make the land 70 parallel to the bracket lingual surface for adequate retention, but as illustrated, the land surface 70 preferably is inclined at between 10° and 20°, more preferably at about 15°, to the parallel position, while the resultant joining surface 72 will be inclined to conform as closely as possible to the shape of retainer member in this position; with the preferred land surface inclinations described above the inclination of surface 72 will usually be at about 15° to 25° to the parallel position and opposite to that of the surface 70. The presence of the land 70 and surface 72 is also found to reduce mechanical interference that otherwise can occur between the retainer member and the junction of the body labial and occlusal surfaces as the retainer member moves between its slot-open and -closed positions, the member being readily moved off the parking land to the slot-closed position.

In use the brackets are fastened to the respective teeth and one end of the arch wire is locked to the end-most bracket by any suitable means (not illustrated). All the retainer members are placed in the slot-open position, the arch wire is inserted into the slots, if possible, and the retainer members are then moved to the slot-closed positions. The retainer members are of adequate strength and rigidity to retain the wire in the slots but permit free movement of the bracket along the wire and, with circular cross-sections, will allow various rotations of the bracket relative to the wire. Any force tending to urge the arch wire out of the slot forces it against the inclined surface of the inwardly-protruding part of the retainer member labial portion, resulting in a force at all times positively urging the retainer member to move to the slot-closed position, at least considerably reducing, if not completely eliminating, the possibility that under the extremely arduous and unpredictable conditions to which the apparatus is subjected, any of the retainer members can spring open and allow the arch wire to escape. It has been found with a particular embodiment that the force required to open the slot is about 9-10 times the force required to close it.

Referring now to FIGS. 5, 7, 9 and 10, it will be seen that a circular cross-section wire of the size intended to be used in the slot 42 is engaged by the end of the member protruding into the slot, while the slot is sufficiently deep to accommodate a rectangular cross-section wire, so that either can be employed with the same bracket. FIG. 6 illustrates the fact that the springy retainer member is able to operate with a wire that is skewed in the slot and partly protruding therefrom, and will apply a desired rotation force to the bracket and the tooth, obviating the need in many instances of the use of a wide double bracket as illustrated in my prior patent specification.

The brackets of the invention are particularly suited for use with rectangular arch wires, in that such a wire is retained in the slot against rotation about its own longitudinal axis, and the wire and springy retainer member are able to cooperate in applying torque to the bracket body and thus to the tooth, extending the nature and type of corrective force that the orthodontist is able to apply with a single bracket. This extended application is facilitated by use of a wire 44 of cross-section as illustrated by FIG. 7, which is provided in its labial face closely adjacent to the junction of the labial and gingival faces with a v-shaped groove constituted by a "parking land" gingival groove face 76 (FIG. 7) and a connecting labial groove face 78, the latter face conforming to the shape of the adjacent part of member 50, and into which groove the retainer member free end 58 can protrude with its extreme end face butting over its entire surface against the land 76. The groove in the wire provides an improved positive connection between the wire and the springy retainer member, and thus between the wire and the bracket body, the inclination of the face 78 assisting in maintaining the retainer member in the slot-closed position.

The considerable extension of the body part beyond the slot to provide the gingival slot surface 60 ensures that the retainer member end 58 is always shielded against the possibility of snagging, or being snagged, even when the part 50 has been forced away from the body by an arch wire that is skewed in the slot, as illustrated by FIG. 6. Moreover, this surface facilitates the insertion of a wire into the slot, since the wire can be moved in the gingival direction to engage the surface and then slid along the surface into the slot. FIG. 8 illustrated the procedure if the wire cannot be inserted in the slot of one bracket. Each bracket is provided with a mesial-distal extending passage 74 of rectangular cross-section at the junction of the body lingual and occlusal surface portions, through which passage a tie wire 76 can be passed to secure the wire to the bracket. The passage 74 could be of any suitable cross-section if it is required only to pass a thin tie wire, but it is found advantageous to make this passage also of rectangular cross-section so that a rectangular cross-section wire placed therein is constrained against rotation relative to the bracket. Such wires can therefore be employed to provide additional corrective forces.

FIGS. 11, 12A–12C show an embodiment of the invention intended for use with a generally rectangular cross-section arch wire 80 of the invention. In order to increase the torque available by use of this wire its width is made such that, when fully inserted in the slot 42, there is present some small lateral displacement of the retainer member away from the bracket body, so that the spring force of the retainer member is applied between the wire and the body.

As illustrated, the preferred cross-section of the wire is with a convex curved labial face 82 and with an occlusal face 84 longer than the gingival face 86 and a lingual face 88 inclined lingually toward the occlusal face, the junction 90 of the occlusal and labial faces extending further in the labial direction than the junction 92 of the gingival and labial faces. The inclined lingual face cooperates with the occlusal face so as to form a tapered wedge-shaped profile terminating in a tip 94 at the junction of the faces. The lingual surface of the slot 42 is inclined lingually to conform with the inclination of the lingual face 88. A clearance is provided between the wire and the slot in the gingival-occlusal direction, so that the wire is capable of a small degree of rotation in the slot. The clearance also permits the wire to be more readily inserted into and withdrawn from the slot. FIG. 12A illustrates the manner in which the engagement of the springy retainer member with the arch wire will apply a positive rotating torque to the bracket 20 and thus to the tooth to which it is attached, as illustrated by the arrows, while FIG. 12C illustrates the manner in which this engagement can apply a negative torque to the bracket and thus to the tooth. The effect in both cases is for the wedge-shaped portion of the arch wire to be moved into snug engagement with the corresponding-shaped portion of the slot 42.

FIGS. 11, 12A–12C also illustrate how the bracket can be modified to be used with the rectangular cross-section arch wire to cause the required tooth movements. Thus the slot 42 can be inclined from the horizontal neutral position shown in FIG. 12B and in solid lines in FIG. 11 to any of a number of inclined positions, clockwise as shown in FIG. 12A and in chain broken lines in FIG. 11, or anti-clockwise as shown in FIG. 12C and in broken lines in FIG. 11. With the clockwise-rotated slot of FIG. 12A the arch wire will apply a positive torque to the bracket until the tooth surface is inclined at a predetermined angle to the vertical, while with the anti-clockwise rotated slot of FIGS. 12C the wire will apply a negative torque to the bracket. The orthodontist can be provided with a selection of brackets in which the slots are at different inclinations at predetermined intervals, extending over a range of positive angles through zero (neutral) and over a range of negative angles, the orthodontist selecting the bracket with the angle required to achieve the desired tooth orientation.

It will be noted that as the slot is rotated clockwise from the neutral position of FIG. 12B its width is increased, while its width is decreased upon anti-clockwise rotation to the negative torque configuration of FIG. 12C, this effect being progressive with the change in torque angle. If the lingual wall of the slot 42 were maintained uninclined as shown in FIGS. 2-6 and 8-10, then at some rotation of the slot its width would become such that a circular cross-section arch wire 46 would be free to move laterally therein, so that it would not be positively contacted by the retainer 20 to enable use to be made of the springyness of the retainer member and its relative sensitivity to lateral displacement. The wedge-shaped configuration of the occlusal-labial junction permits this undesirable effect to be avoided, and it is found possible with all the required bracket configurations to provide for adequate engagement between the wire 46 and the retainer 50, the wire being urged by the retainer to the wedge-shaped portion of the slot 42.

I claim:

1. An orthodontic bracket comprising a bracket body having lingual, labial, gingival, occlusal, distal and mesial surface portions and a mesial-distal extending arch wire slot opening to the labial surface portion, and a retainer member of resilient material having opposed labial and lingual portions thereof in embracing sliding engagement with corresponding labial and lingual body surface portions, the retainer member being movable on the body between two positions in which the labial side of the slot is respectively open and closed, characterized in that the free end of the retainer member labial portion, extends toward the lingual so that in the slot-closed position it protrudes into the arch wire slot so as to engage an arch wire therein and urge it towards the lingual and occlusal walls of the slot, movement of the retainer member away from the slot-closed position toward the slot-open position taking place against the resilience of the retainer member owing to movement apart of the said opposed portions thereof by the interposed engaged part of the bracket body as the said free end of the protruding labial portion is moved out of the arch wire slot.

2. A bracket as claimed in claim 1, characterized in that the said protruding free end of the labial portion protrudes progressively further along its length toward the free end into the arch wire slot from the occlusal to the gingival direction for said engagement with an arch wire in the slot, whereby reaction of the arch wire against the protruding labial portion urges the retainer member toward the slot-closed position.

3. A bracket as claimed in 1 or 2, characterized in that the portion of the body providing the labial surface includes a mesial-distal extending parking land disposed occlusally of the said arch wire slot and receiving the retainer member labial portion in the slot-open position and retaining the member in that position.

4. A bracket as claimed in claim 1 or 2, characterized in that the portion of the body providing the labial surface includes a mesial-distal extending parking land disposed occlusally of the said arch wire slot, the said parking land comprising a gingival surface receiving the free end of the retainer member labial portion in the slot-open position and retaining the member in that position.

5. A bracket as claimed in claim 1 or 2, characterized in that the bracket body part not embraced by the retainer member has an increased labial-gingival dimension adjacent the slot to provide a gingival surface extending beyond the slot and engaged by the free end of the retainer member labial portion in the slot-closed position, the last mentioned bracket body part shielding the said retainer member free end against snagging.

6. A bracket as claimed in claim 1 or 2, characterized in that the bracket body part not embraced by the retainer member has a considerably increased labial gingival dimension to provide adjacent the slot a labially-extending step with a gingival surface engaged by the free end of the retainer member labial portion in the slot-closed position to prevent movement of the retainer member beyond that position, the said gingival surface being engagable by an arch wire as it is inserted in the slot to guide the wire into the slot.

7. A bracket as claimed in claim 1 or 2, characterized in that the part of the bracket body not embraced by the retainer member has an access recess opening to the lingual and gingival surfaces, into which recess an end of the retainer member lingual portion extends, whereby the retainer member can be moved from slot-closed position to slot-open position by insertion of a tool into the access recess and engagement thereof with the end of the retainer member lingual portion.

8. A bracket as claimed in claim 1 or 2, characterized in that the bracket body part embraced by the retainer member is provided at the junction of the lingual and occlusal surfaces with a mesial-distal extending passage adapted to receive a retainer wire.

9. A bracket as claimed in claim 1 or 2, characterized in that the bracket body part embraced by the retainer member is provided at the junction of the lingual and occlusal surfaces with a mesial-distal extending passage of rectangular cross section adapted to receive a retainer wire.

10. A bracket as claimed in claim 1 or 2, characterized by combination with a cementing pad attached thereto covering the lingual surface and providing a respective lingual surface for reception of cement to fasten the bracket to a tooth surface.

11. A bracket as claimed in claim 1 or 2, characterized by combination with a tooth-embracing band to which the bracket is fixed.

12. A bracket as claimed in claim 1 or 2, characterized in that the part of the retainer member in engagement with the lingual body surface has a part thereof displaced out of its general plane and engagable with a cooperating part of the bracket body to determine the slot-open position of the retainer member.

13. A bracket as claimed in claim 1 or 2, characterized in that the said mesial-distal arch wire slot has parallel occlusal and gingival faces and a lingual face that is inclined lingually in the gingival to occlusal direction, and in combination with an arch wire which extends mesially-distally through the arch wire slot and has a labial face that is engaged by the said protruding labial portion of the retainer member, the said arch wire having a convex curved labial face, and having a lingual face that is lingually-inclined in the direction from the gingival face to the occlusal face at an inclination corresponding to that of the slot lingual face and so as to form a wedge-shaped profile at the junction of its lingual and occlusal faces.

14. A bracket as claimed in claim 1 or 2, characterized in that the said mesial-distal arch wire slot has parallel occlusal and gingival faces and a lingual face that is inclined lingually in the gingival to occlusal direction, and in combination with an arch wire which extends mesially-distally through the arch wire slot and has a labial face that is engaged by the said protruding labial portion of the retainer member, the said arch wire having a convex curved labial face, and having a lingual face that is lingually-inclined in the direction from the gingival face to the occlusal face at an inclination corresponding to that of the slot lingual face and so as to form a wedge-shaped profile at the junction of its lingual and occlusal faces, the arch wire occlusal face being parallel to the gingival face and longer than the gingival face with the junction of the occlusal and labial faces extending further in the labial direction than the junction of the gingival and labial faces so as to provide the said wedge-shaped profile.

15. An orthodontic arch wire for use in combination with an orthodontic bracket comprising a bracket body having lingual, labial, gingival, occlusal, distal and mesial surface portions and a mesial-distal extending arch wire slot opening to the labial surface portion, and a retainer member of resilient material having opposed labial and lingual portions thereof in embracing sliding engagement with corresponding labial and lingual body surface portions, the retainer member being movable on the body between two positions in which the labial side of the slot is respectively open and closed, the said mesial-distal arch wire slot having parallel occlusal and gingival faces and a lingual face that is inclined lingually in the gingival to occlusal direction, the said arch wire having a convex curved labial face, and having a lingual face that is lingually-inclined in the direction from the gingival face to the occlusal face at an inclination corresponding to that of the slot lingual face and so as to form a wedge-shaped profile at the junction of its lingual and occlusal faces.

16. An arch wire as claimed in claim 15, wherein the arch wire occlusal face is parallel to the gingival face and longer than the gingival face with the junction of the occlusal and labial faces extending further in the labial direction than the junction of the gingival and labial faces so as to provide the said wedge-shaped profile.

* * * * *